(12) United States Patent
Mucci et al.

(10) Patent No.: US 9,217,706 B2
(45) Date of Patent: Dec. 22, 2015

(54) MOBILE SMART DEVICE INFRARED LIGHT MEASURING APPARATUS, πMETHOD, AND SYSTEM FOR ANALYZING SUBSTANCES

(71) Applicant: Quick LLC, Farmington, NY (US)

(72) Inventors: David Anthony Mucci, Farmington, CT (US); Ronald Gary Clark, Jr., Southbury, CT (US); James Scott Fox, Farmington, CT (US)

(73) Assignee: QUICK LLC, Farmington, CT (US)

( * ) Notice: Subject to any disclaimer, the term of this patent is extended or adjusted under 35 U.S.C. 154(b) by 73 days.

(21) Appl. No.: 13/929,882

(22) Filed: Jun. 28, 2013

(65) Prior Publication Data

US 2014/0027641 A1  Jan. 30, 2014

Related U.S. Application Data

(60) Provisional application No. 61/665,684, filed on Jun. 28, 2012.

(51) Int. Cl.
| | |
|---|---|
| *G01J 3/02* | (2006.01) |
| *G01N 21/3577* | (2014.01) |
| *A61B 5/00* | (2006.01) |
| *A61B 5/1455* | (2006.01) |

(52) U.S. Cl.
CPC .......... *G01N 21/3577* (2013.01); *A61B 5/0075* (2013.01); *A61B 5/14552* (2013.01); *G01J 3/0272* (2013.01)

(58) Field of Classification Search
USPC .................................................. 250/339.07
See application file for complete search history.

(56) References Cited

U.S. PATENT DOCUMENTS

| | | | |
|---|---|---|---|
| 3,794,425 A | 2/1974 | Smith et al. | |
| 5,313,941 A * | 5/1994 | Braig et al. | 600/322 |
| 5,361,758 A | 11/1994 | Hall et al. | |
| 5,519,219 A * | 5/1996 | Alexay et al. | 250/339.07 |
| 6,236,047 B1 | 5/2001 | Malin et al. | |
| 8,309,931 B2 | 11/2012 | Buffington et al. | |
| 8,406,839 B2 | 3/2013 | Kaushal et al. | |
| 2006/0122801 A1 | 6/2006 | Dietiker | |

(Continued)

FOREIGN PATENT DOCUMENTS

WO   2012/055047 A1   5/2012

OTHER PUBLICATIONS

"International Search Report", PCT International Search Report (Oct. 22, 2013), PCT/US2013/048415, 2 pgs.

(Continued)

*Primary Examiner* — Christine Sung
(74) *Attorney, Agent, or Firm* — Ascenda Law Group PC

(57) ABSTRACT

A handheld infrared spectroscopy device and method of use. The device is a hand-held spectroscopy device, that may be integral to a mobile phone or smart device such as a smart phone, tablet, personal digital assistant, computer or other device that is portable and capable of performing applications. A liquid sample port internal to the device and in close proximity to the device spectrometer performs infrared spectra analysis on liquid samples, allowing both portability as well as highly sophisticated and specific spectral analysis of liquid samples. The device has wireless communication capability, enabling transmission of data and spectral imagery across the globe.

7 Claims, 15 Drawing Sheets

(56) References Cited

U.S. PATENT DOCUMENTS

2013/0248695 A1* 9/2013 Macintyre et al. ....... 250/227.11
2013/0265568 A1* 10/2013 Micheels et al. ................ 356/51

OTHER PUBLICATIONS

Hans; et al., "IrSens: Sensing cocaine in saliva employing a one-step extraction and MIR spectroscopy", Nano-tera.ch (RTD 2009), poster downloaded Feb. 5, 2015 from: http://www.nano-tera.ch/pdf/posters2011/0-0-3-1.png, 1 pg.

Jacoby; et al., "Determination of the Glycoforms of Human Chorionic Gonadotropin β-Core Fragment by Matrix-assisted Laser Desorption/Ionization Time-of-Flight Mass Spectrometry", Clin Chem (Nov. 2000), 46(11):1796-1803.

Katsumoto; et al., "Usefulness of a curve fitting method in the analysis of overlapping overtones and combinations of CH stretching modes", J Near Infrared Spectrosc (2002), 10(1):85-91.

Khaustova; et al., "Noninvasive biochemical monitoring of physiological stress by Fourier transform infrared saliva spectroscopy", Analyst (Dec. 2010), 135(12):3183-92.

Ridder; et al., "Noninvasive alcohol testing using diffuse reflectance near-infrared spectroscopy", Appl Spectrosc (Feb. 2005), 59(2):181-9.

Scott; et al., "Diabetes-related molecular signatures in infrared spectra of human saliva", Diabetol Metab Syndr (Jul. 2010), 2:48, 9 pgs.

Shaw; et al., "Infrared Spectroscopy in Clinical and Diagnostic Analysis", Encyclopedia of Analytical Chemistry (2006), 20 pgs.

* cited by examiner

MOBILE SMART DEVICE INFRARED LIGHT MEASURING APPARATUS, πMETHOD, AND SYSTEM FOR ANALYZING SUBSTANCES

CROSS-REFERENCE TO RELATED APPLICATIONS

This application claims the benefit of U.S. Provisional Patent Application No. 61/665,684, filed on Jun. 28, 2012. The prior application is incorporated by reference.

FIELD OF THE INVENTION

The present invention relates to infrared absorption spectroscopy, and more particularly to performing infrared spectroscopy solution analysis on a mobile platform using a smart device, or a separate hand-held mobile device that may be hard-wired or wirelessly attached to a smart device or computer for additional data analysis, transmission and communication. The device and method make remote and 'field' testing of solution samples easy and efficient, with the ability to analyze and share the data globally.

BACKGROUND OF THE INVENTION

Infrared absorption spectroscopy is growing technology and gaining acceptance in a variety of applications in numerous fields, particularly, the medical and law enforcement fields. Absorption spectroscopy is useful in chemical analysis because of its specificity and its quantitative nature. Also called Fourier Transform infrared spectroscopy, this method of IR spectroscopy measures the amount of infrared light that is transmitted through a sample. Infrared light interacts with the chemical bonds in organic and inorganic materials, and the bonds in such materials will absorb varying intensities of infrared light at varying frequencies. An IR spectrometer registers the infrared light that is absorbed by a material and displays it in a form called an infrared spectrum. The infrared spectral region ranges from a wavelength of about 650 nm, at the red end of the visual spectrum, to a wavelength of about 1 mm, at the microwave region of the spectrum. This wavelength range may be further subdivided into near-infrared (about 650 to about 1400 nm), short infrared (about 1400 to about 3000 nm), mid-infrared (about 3000 to about 8000 nm), long infrared (about 8000 to about 15000 nm), and far infrared (greater than 15000 nm to about 1 mm). Frequently, the near-IR and short-IR ranges depicted herein are referred to generally as "near-IR" with a range of about 650 nm to about 3000 nm. Infrared wavelengths are frequently expressed in units called wavenumbers, expressed as "$cm^{-1}$" which is the number of waves that fit into a centimeter.

Absorbance bands, or "peaks" that occur at certain wavelengths or wavenumbers represent absorbance of IR light at those wavelengths by molecules as a result of their chemical bonds. As a result, infrared spectroscopy is a technique frequently used to identify molecules and quantify their presence by analysis of their constituent bonds. Each chemical bond in a molecule vibrates at a frequency which is characteristic of that bond. A group of atoms in a molecule (e.g. $CH_2$) may have multiple modes of oscillation caused by the stretching and bending motions of the group as a whole. If an oscillation leads to a change in dipole in the molecule, then it will absorb a photon which has the same frequency. The vibrational frequencies of most molecules correspond to the frequencies of infrared light. Typically, the technique is used to study organic compounds using light radiation from about 4000 to about 400 $cm^{-1}$, representing the mid-infrared spectral range. A spectrum of all the frequencies of absorption in a sample is recorded. This can be used to gain information about the sample composition in terms of chemical groups present and also its purity (for example a wet sample will show a broad O—H absorption around 3200 $cm^{-1}$).

When analyzing synthetic and natural materials, near IR absorption spectroscopy has recently shown unprecedented industrial success in multiple applications in grains, forages, baking products, flour, beverages, feeds, pharmaceuticals, dairy products, hydrocarbons and petrochemicals, fine chemicals, radioactive and hazardous materials, and medical imaging and diagnostics. The basic uses of near infrared spectroscopy have been for process control, for quality assessment, for identification of raw materials and process byproducts, and for chemical quantitative analysis of complex mixtures.

To evaluate the presence and quantity of molecules and substances present in a sample, infrared light is passed through the sample. The intensity of the infrared spectra that passes through the sample provide quantitative information (e.g. from the size of the peaks of light measured), and the frequencies of the wavelengths at which absorption takes place in the sample identifies the presence of certain compounds, as no two compounds have the same atomic makeup, thereby producing different frequencies of vibrations between bonds of the atoms making up the material, providing qualitative information about substances in the sample, based on the molecular structures and bonds in the substances. The IR test thus provides a molecular "fingerprint" of the substances present in a tested sample. Generally, for the analysis of clinical specimens, infrared spectra data and reference assays are generated, to serve as calibration samples. Calibration samples permit the identification of specimens that are known, and libraries of calibration samples can also be used to identify unknown substances in the test samples. IR spectroscopy has been growing in its use to detect drugs, such as cocaine in saliva, to detect glucose in diabetes patients, and also to detect biochemical changes in patients, which may be used to detect disease. Near infrared spectroscopy has also been used to test for various compounds in ponds and wetlands.

Additional information concerning infrared spectroscopy related art can be found in the following publications, each of which is fully incorporated herein by reference: T. D. RIDDER,* S. P. HENDEE, and C. D. BROWN, Noninvasive Alcohol Testing Using Diffuse Reflectance Near-Infrared Spectroscopy, APPLIED SPECTROSCOPY, Volume 59, Number 2, 2005; Y. Katsumoto, D. Adachi, H. Sato, and Y. Ozaki, J. Near Infrared Spectrosc. 10, 85 (2002); Y. Katsumoto, D. Adachi, H. Sato, and Y. Ozaki, J. Near Infrared Spectrosc. 10, 85 (2002); and Eli S. Jacoby, Andrew T. Kicman, Paul Laidler and Ray K. Iles, Determination of the Glycoforms of Human Chorionic Gonadotropin β-Core Fragment by Matrix-assisted Laser Desorption/Ionization Time-of-Flight Mass Spectrometry; David A Scott, Diane E. Renaud, Sathya Krishnasamy, Pinar Meric, Nurcan Buduneli, Svetki Cetinkalp, Kan-Zhi Liu, Diabetes-related molecular signatures in infrared spectra of human saliva, Diabetology & Metabolic Syndrome 2010, 2:48.; Kerstin M. C. Hans, Susanne Muller, Markus W. Sigrist, IrSens: Sensing cocaine in saliva employing a one-step extraction and MIR spectroscopy, available at http://www:nano-teosters2011/0-0-3-1.png; R. Anthony Shaw and Henry H. Mantsch, Infrared Spectroscopy in Clinical and Diagnostic Analysis, Encyclopedia of Analytical Chemistry; Svetlana Khaustova, Maxim Shkurnikow, Evgeny Tonevitsky, Viacheslav Artyushenko, Alexander Tonevitsky, Noninvasive biochemical monitoring of physiological stress by Fourier Transform infrared saliva spectroscopy, The Royal Society of Chemistry, 2010, Received 16 Jul. 2010, accepted 29 Sep. 2010; Steve Barnett, White Paper: Evaluation of Near-IR Wavelengths for the Detection of Glucose, Acetone, and Ethanol in Saliva.

Currently, the devices and methods available for detection, quantification and analysis of constituents in body fluids or other environmental samples using infrared spectroscopy require drying the samples or other sample manipulation, laboratory apparatus (not portable or field-ready), or measurements from live subjects, subject tissue, etc. For example, U.S. Pat. No. 8,309,931 is directed to rapid methods for diagnosing disease states such as bladder pain syndrome and interstitial cystitis using infrared spectroscopy. However, the method requires collecting a sample, depositing a fraction of the sample on a slide, drying the fraction, and collecting IR spectra to identify the test subject's condition compared to various data models. U.S. Pat. No. 8,406,839 is directed to a handheld device for measuring the concentration of a compound and a value of oxygen saturation in the blood or part of a subject, such as a human or animal. U.S. Pat. No. 5,361,758 is directed to a non-invasive device for measuring the concentration of glucose and other constituents in the blood and tissue of a living human or animal. U.S. Pat. No. 6,236,047 is also directed to non-invasive method of determining blood glucose concentration in a living thing.

What remains lacking in the field of infrared spectroscopic analysis is a device and method for providing clinical precision in liquid samples which can be in remote locations (away from the clinic or laboratory), whereby the device and method operate to isolate focused single or multiple, narrow and wide bandwidths of infrared light for a more accurate identification and quantification of compounds in the samples. The devices and method of the present invention create this ability providing IR spectroscopic sample testing in liquid or solution format to mobile/handheld device platforms.

SUMMARY

What is contemplated according to one embodiment of the invention is a handheld device integrated with a liquid sample test port and spectrometer for spectroscopic analysis. The infrared spectrometer may be operably connected to a processor, which may be a microprocessor, computer, etc. The liquid sample test port is preferably in close proximity to the infrared light source of the spectrometer, and the handheld device is preferably capable of wireless communication via a wireless communication network.

According to one embodiment of the invention, a handheld spectroscopy device comprises an infrared light source that emits a wavelength of light in the infrared range, a liquid sample test port and sample tray for receiving a liquid sample, the liquid sample test port and sample tray in close association with the infrared light source wherein the infrared light is directed through all or part of the sample on the sample tray, an infrared receiver for recording a spectrum of the frequencies of infrared light absorption by the liquid sample, and a data processor connected to the infrared light receiver to detect and quantify the concentration of one or more compounds in the liquid sample in the form of spectral data and/or image.

According to another embodiment of the invention, a method for determining a concentration of one or more compounds in a liquid sample comprises placing the liquid sample on a sample tray, inserting the sample tray into a sample test port housed in a handheld device containing an infrared spectrometer, directing infrared light at the sample, recording a spectrum of the frequencies of infrared light absorption, and determining the presence or concentration of one or more compounds in the liquid sample based on the sample infrared light absorption.

According to yet another embodiment of the invention, a method for determining a concentration of one or more compounds in a bodily fluid using infrared spectroscopy comprises placing a sample of the bodily fluid on a sample tray, inserting the sample tray into a sample test port housed in a handheld device containing an infrared spectrometer, directing infrared light at the sample, detecting wavelengths of infrared light as result of infrared light absorbed by the sample, recording a spectrum of the frequencies of infrared light absorption by the sample, and transmitting the spectrum of the frequencies of infrared light absorption by the sample via wireless communication network from the handheld device to one or more other devices.

According to yet another embodiment of the present invention, a method of testing a liquid sample using infrared spectroscopy to detect or quantify one or more substances in the liquid sample comprises receiving a liquid sample in a liquid test port slideably connected to a handheld spectroscopy device, exposing the liquid sample to infrared light at close range, recording a spectrum of the frequencies of infrared light absorption by the sample, analyzing the frequencies of absorption to detect or quantify the one or more substances in the liquid sample to generate spectral data associated with the liquid sample, and transmitting the spectral data via wireless communication network from the handheld device to one or more other devices.

This device and method of the current invention are useful for highly specific qualitative and quantitative analysis of substances present in and changes that occur in bodily fluids, other fluids or materials such as animal fluids, or environmental samples. Users can test any organic or inorganic liquid samples virtually anywhere in the world without having to otherwise manipulate (e.g. dry) or transport samples to the laboratory setting—the testing and spectroscopy analysis can be done in real time in the field.

The device comprises an infrared spectrometer as part of a small hand-held dedicated spectroscopy device or as part of a smart device. If the IR spectrometer is part of a smart device, the device is modified to house the IR spectrometer internally, similar to, for example, the internal camera of a commercially available smart phone or smart device. A liquid sample test port, similar to a USB or charging port of most smart devices and computers is designed internal to the device housing to receive a small sample tray that, preferably, slideably engages with the spectroscopy device. As used herein, the term "infrared (or IR) spectrometer" or "infrared (or IR) spectroscopy device" most generally means an instrument that emits and detects wavelengths of light in the infrared light range. The components that make up the spectrometer include (but are not limited to) the infrared light source, or emitter, an infrared light receiver, and preferably one or more infrared light filters. According to one embodiment of the present invention, the spectrometer is incorporated in the handheld device or smart device such that the infrared light emitter is in close proximity with the liquid sample test port so that the spectrometer is strategically aligned to transmit the infrared light through a liquid sample on the sample tray when the tray is slid into the device via the port. The infrared receiver portion of the IR spectrometer is strategically aligned on the opposite side of the sample tray from the infrared light emitter or on the same side of the tray as the emitter, if on the same side, transmitting the infrared light through the sample via a reflecting arrangement, as commonly understood in the spectrometry community. The infrared spectrometer is preferably compact in nature and may be any commercially available spectrometer that is small enough to be installed in the handheld device or a smart device.

This spectroscopy device may use infrared filters to block unwanted light radiation and to allow only IR radiation to pass through. Specific band or bandwidth filters, sometimes called "band pass" filters may be used to focus only infrared light with certain wavelengths or bands to pass through the sample. Infrared light is transmitted by the IR emitter through one or more filters, either before or after IR light is transmitted through the sample on the sample tray. Said another way, the filters may be operably placed closer to the IR emitter and/or the IR receiver. The resulting spectral data can then be evaluated and compared to, for example, calibration data for particular analytes or spectroscopy libraries built into the device or available through wireless communication. The spectral data can also be used to generate calibration data. The infrared spectrometer may be operably connected to a microprocessor that analyzes the wavelength measurements transmitted through the sample, producing data and/or a spectral images identifying one or more substances or constituents in the sample, and quantifying the levels of the one or more substances or constituents in the sample. The data/image output from the microprocessor may be displayed on the handheld device or smart device, stored by the microprocessor in the device for future use (for example, comparison to other sample data), transmitted to another device or transmitted to a printer. The microprocessor may be mounted in the same housing as the spectrometer, and a wireless data transmission unit may also be mounted in the housing for transmitting or receiving data from the microprocessor as well as transmitting and receiving data to/from external devices. The device may also have a battery or other power source. According to one embodiment, the handheld spectroscopy device is a small, portable, desk-top type device that has a USB connection to a computer or other smart device or mobile phone, and a plug for AC power. The device may also be provided with wireless capability and may have a battery for wireless operation. The device may have buttons for on/off, test, send/receive (for sending and receiving data) and a display. Wireless transmission modalities contemplated by the current invention include but are not limited to: Bluetooth, Wi-Fi, personal area network, near field communications, cellular telecommunications, satellite telecommunications.

According to one embodiment of the invention, the handheld device may be a cell phone, personal digital assistant, smart device, smart tablet, laptop computer, or other portable device that has an integrated spectrometer, microprocessor, and wireless communications capability.

In various modes of operation, the invention provides the ability to qualitatively and quantitatively determine spectral analysis for one or more substances in solution or in multiple solutions in a hand-held device that does not need to be in close proximity to the source of the sample, or a laboratory or clinic. Samples may be taken and tested immediately, for example, a roadside saliva test for drug/DUI testing, a urine test for pregnancy testing, or rapid testing of environmental, e.g. water, samples to test for toxins or dangerous chemicals where issues of time, substance degradation, sample evaporation, etc. may be a concern.

It will be appreciated by those skilled in the art that embodiments of the disclosed inventions may include a computer program accessible to and/or executable by a processing system, e.g. a one or more data processors and memories that may be part of, or connected to, the spectroscopy device. The processors and/or memories carrying out the steps of analyzing the wavelengths of absorbed infrared light may be part of a spectroscopy device that is integral to a smart phone or smart device, or part of a handheld spectroscopy device in communication with one or more other devices with processing capabilities. Steps of the disclosed method, including but not limited to wavelength measurement, wavelength analysis, interferent determination and/or calibration constant generation, may be stored as one or more computer readable code segments or data compilations on a computer readable carrier medium, which may include a thumb drive, hard disk, CD/DVD or hard programmed into a processor that is part of the device itself.

The current invention has the ability to specifically receive and record data at specific wavelengths in specific focused bands of nanometers of infrared light, such bands ranging for example, from 1 nanometer wide to as much as 1000 nanometers wide, the wavelengths being typically in the mid- and near-IR wavelength ranges. The invention is not limited with respect to receiving and analyzing/recording multiple different bandwidths of IR light, which is advantageous for the detection and quantification of multiple constituents in a test sample. The test liquid samples are basically tested in a "microscope" type fashion without having to be in a laboratory or clinical setting. Also, GPS or cellular-triangulation can be programmed into the device to enable the device with location sensing/stamping and time stamping capabilities. According to another embodiment, the device is capable of, or connected to a device that enables location sensing/stamping and time/stamping of the spectral data and imagery recorded by the device.

BRIEF DESCRIPTION OF THE FIGURES

The invention will be more fully understood by reference to the following figures which are for illustrative purposes only.

DETAILED DESCRIPTION OF THE EMBODIMENTS

Figure 1:
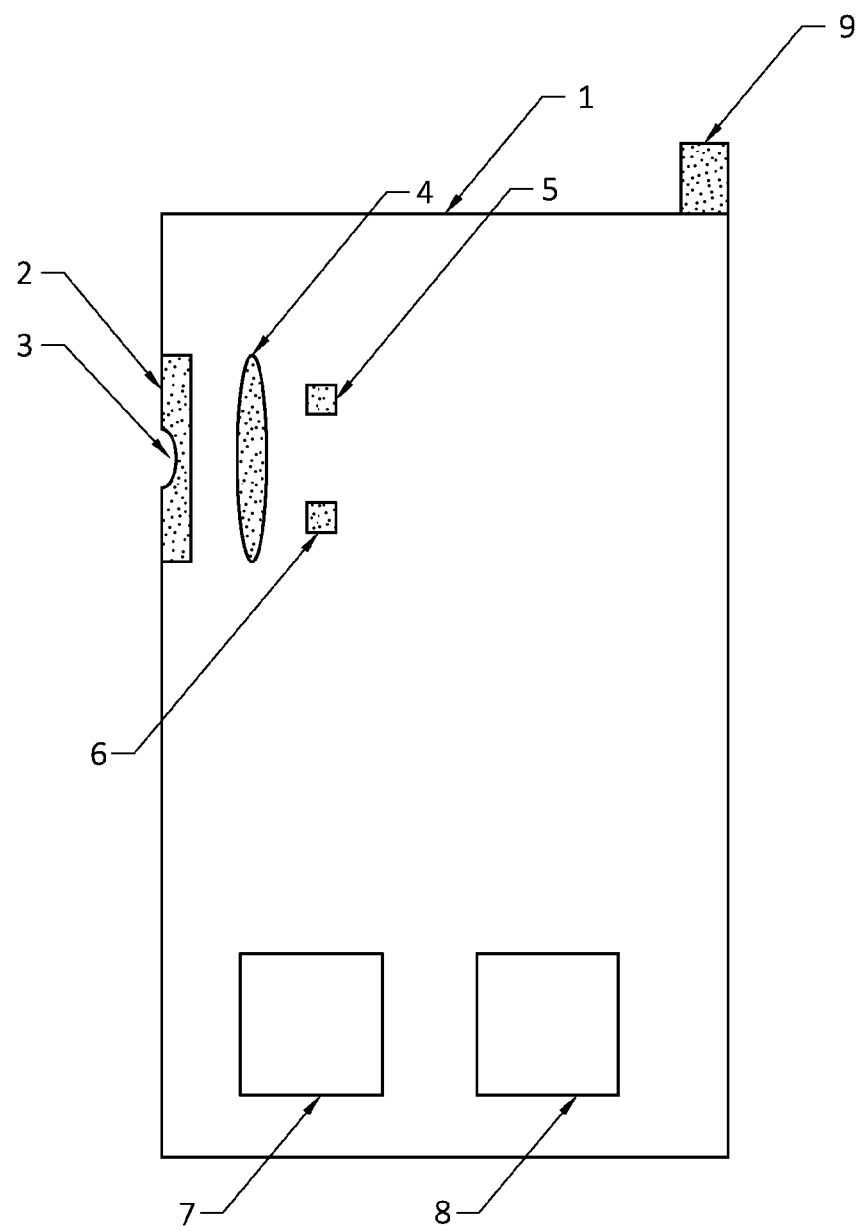
FIG. 1 is an illustrative view of a spectroscopy device of the present invention with the spectrometer integrated with a smart phone.

The present invention is directed to a handheld infrared spectroscopy method and device. The handheld device may be a smart device. A housing holds the spectroscopy apparatus, including the infrared emitter, one or more filters, infrared receiver, as well as optional data processor and data transmitter features. The housing also has a liquid test sample port and a test sample tray. The housing may also contain a battery or other power source with plug-in charging capability. The data transmitter may be a wireless communication device that is associated with a wireless communication network such as near field communication, Wi-Fi, Bluetooth or other wireless communication network. Alternatively, the data may be transmitted by the device via a USB connection to another computer or device. The sample tray is preferably made of material such as polyethylene plastic, glass, Plexiglas, plastic and/or any other material transparent to spectrums of infrared light so that the tray itself does not interfere with the spectrum received from the sample after IR transmission. The sample tray has an opening at the tip and a vent hole at the other end so that liquid is wicked into a well on the tray using capillary action.

According to the method, a sample to be tested is introduced into the sample tray. The tray is then inserted into the spectroscopy device via the test port. A sample may be small, e.g. 2 microliters, up to several milliliters. An infrared source or emitter sends the infrared light beam through the sample directly or by reflection, based on the internal configuration of the spectroscopy system (e.g. system fitted with an internal-reflection element, such as a lens), using a standard Fourier Transform IR spectrometer or other commercially available IR spectrometer. One or more filters may be used to match the absorption bands anticipated from the test sample. A calibration IR emitter and calibration IR receiver, and one or more calibration filters are used in the device to calibrate the device each time it is used. The calibration emitter may be set at a wavelength different than that being used to test the sample. Infrared light is sent from the calibration emitter through the sample (and any filters) to the calibration receiver. Sample spectra are collected and compared to calibration spectra and/or known analyte spectral data. If a sample of saliva is being tested, saliva is a mixture of many different compounds, thus the infrared spectrum of saliva is a superposition of the individual analyte spectra and intensities of the absorption bands in the spectra are proportional to the concentrations of the components.

The infrared spectroscopy device and method of the present invention utilize infrared light with wavelength in the range of 0 nm to approximately 15,000 nm, more specifically, infrared light with a wavelength in the range of approximately 650 nm to approximately 15,000 nm, more specifically, near infrared light with wavelength in the range of about 650 nm to about 3000 nm, and mid infrared light with a wavelength in the range of about 3000 nm to about 8000 nm. Water absorbs strongly above 3000 nm, so when measuring constituents that can be measured below 3000 nm, a near IR range of 650 to 3000 nm is frequently employed.

For aqueous solutions, it has been found that an optimal distance, or path length from the IR emitter to the sample is about 0.5-2.5 mm, more specifically about 0.75-1.5 mm, more specifically about 0.5-1.0 mm, thus, in accordance with one embodiment of the invention, the sample to be tested will be positioned on the sample tray in close proximity to the IR emitter and receiver. The sample may be positioned in between the emitter and receiver, or a reflectance configuration may be used to reflect the IR light through the sample and to a receiver located in line with the emitter but opposite the sample and sample tray. Existing software as part of the spectrometer used in the current device and method may be used to translate the spectral wavelength data from the test sample into quantitative and qualitative data, including spectral images, that is used to compare to reference data, and to identify the presence of substances and compounds in the test sample. The information generated, the quantitative and qualitative data and imagery may then be transmitted, preferably wirelessly, to one or more devices or locations for further processing, analysis, monitoring, or recordkeeping.

Turning now to the Figures, FIG. 1 illustrates one embodiment of the spectroscopy device integral to a smart device, more specifically this embodiment shows a smart phone 1, and comprises a window 2 with a solution receptacle 3 forming the entrance for the internal liquid test port (not shown in FIG. 1), lens 4, which is used to reflect the IR light from infrared light emitter 5, passed through the sample (not shown in FIG. 1) to infrared light receiver 6 (which aspects and steps occur internal to the smart phone 1). The embodiment of the invention illustrated in FIG. 1 also includes a data processor 7, a GPS unit 8, and a data transmitter/receiver 9, but the specific placement of these features in smart phone 1 will depend on the design of smart phone 1; what is illustrated in FIG. 1 is exemplary only and not limiting of the scope of the invention.

Figures 2A, 2B:
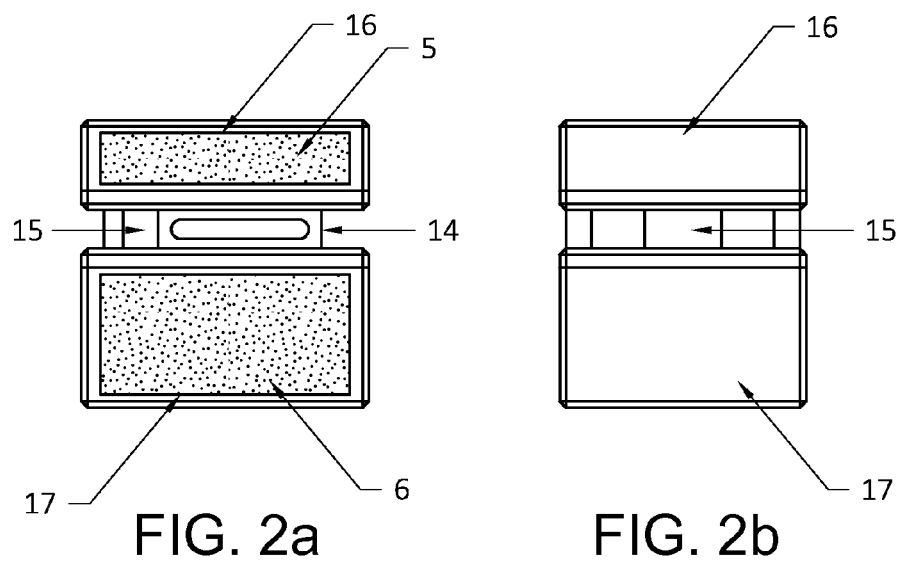
FIGS. 2a and 2b are side views of an exemplary spectroscopy device of the present invention.
Figure 2C:
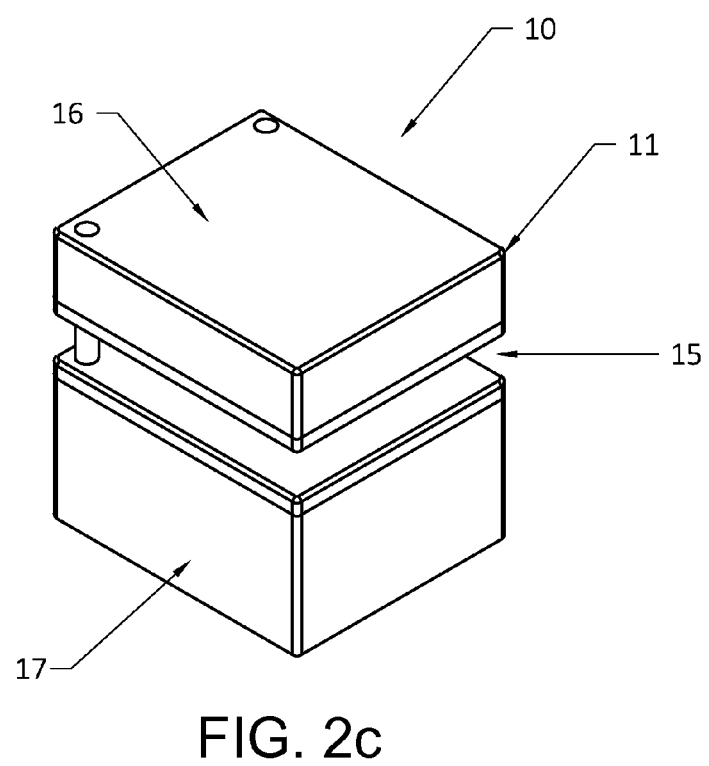
FIG. 2c is a perspective view of the same device.

FIGS. 2a, 2b and 2c illustrate different views of another embodiment of a handheld device of the present invention, Generation Two device 10. This embodiment is small, portable, and shaped like a "cube", and its dimensions may be about 2.4 inches wide by about 2.8 inches long by about 2.8 inches high. Of course, these dimensions are for example only, and therefore do not limit the scope of the invention. FIG. 2a provides a side view of Generation Two device 10, showing sample tray 14 in strategic alignment in liquid test port 15 between the infrared light emitter 5 and infrared light receiver 6 as it would be during operation of Generation Two device 10, so that the infrared light is transmitted through part or all of a liquid sample on the sample tray 14. Infrared light emitter 5 is part of a spectrometer emitter digital board 16 and infrared light receiver 6 is part of a spectrometer receiver digital board 17. FIG. 2b provides a front view of Generation Two device 10, showing test port 15. FIG. 2c shows that Generation Two device 10 comprises an outer housing 11 that houses liquid test port 15, emitter digital board 16, and receiver digital board 17. Digital boards 16 and 17 may also house a microprocessor and other aspects of the invention as discussed herein.

Figure 3:
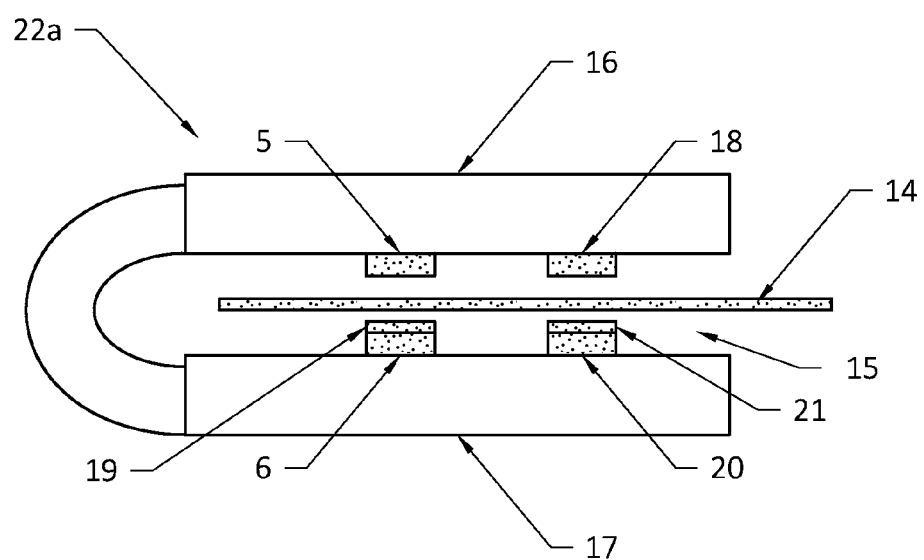
FIG. 3 is an illustrative exemplary side view of the internal design of the spectroscopy device illustrated in FIGS. 2a through 2c.

FIG. 3 illustrates the internal schematics of exemplary embodiments of the invention, specifically one arrangement of a spectrometer 22a, which will operate internally as part of one of the handheld devices contemplated by the present invention. This figure features emitter digital board 16 that houses infrared emitter 5 and a calibration infrared emitter 18. Infrared receiver 6, with an attached band pass filter 19, sit directly opposite the infrared emitter 5. A calibration infrared receiver 20 with an attached calibration band pass filter 21, which are attached to the receiver digital board 17 sit directly opposite calibration infrared emitter 18. Between the emitter digital board 16 and receiver digital board 17 units is sample tray 14 shown as a removable tray that sits operably in liquid test port 15.

Figure 4:
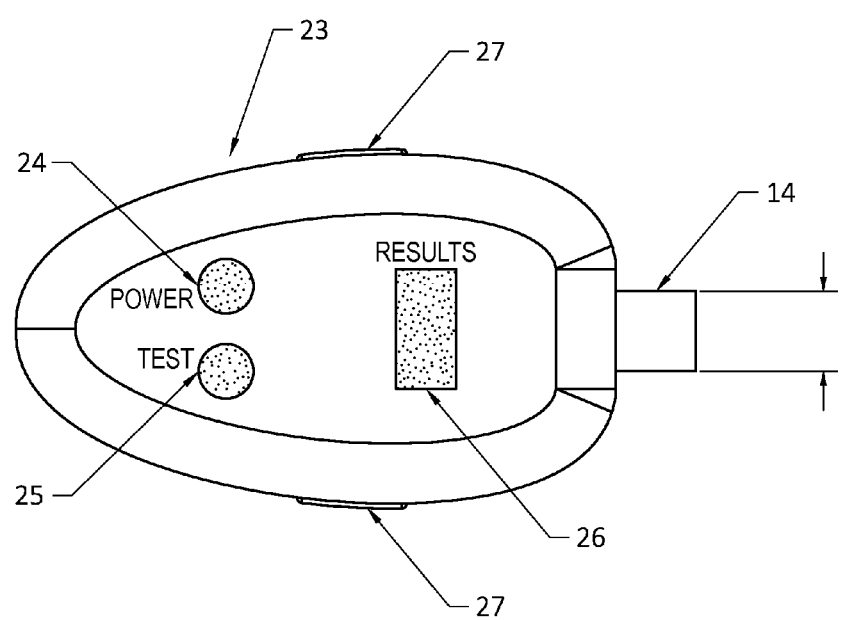
FIG. 4 depicts an exemplary top view of the another embodiment of spectroscopy device contemplated by the present invention.

FIG. 4 is an exemplary top view of one embodiment of Generation Three device 23 in accordance with the invention. This embodiment is small, portable, and shaped like a computer mouse, and may have dimensions as small as about 1.5 inches wide by about 2.5 inches long by about 0.5 inches high. The sample tray 14 shown in this Figure may be as small as about 0.039 inches (1 mm) in depth and about 0.394 inches (10 mm) in width. Of course, these dimensions are for example only, and therefore do not limit the scope of the invention. This figure depicts an on/off button 24, a test/send button 25, a display screen 26 for display of spectral data and/or images. On both sides of Generation Three device 23 are hand grips 27 and sample tray 14 is shown, slid partway into Generation Three device 23.

Figure 5:
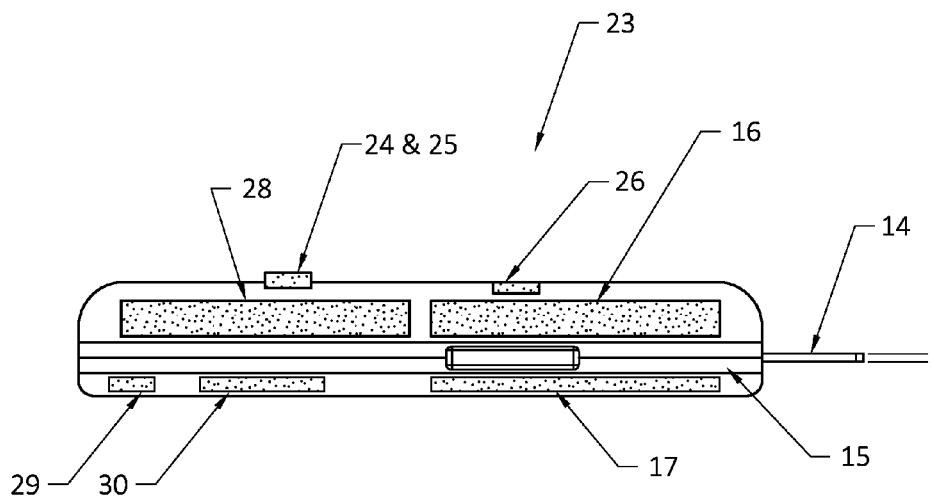
FIG. 5 depicts an exemplary side view of the spectroscopy device illustrated in FIG. 4.

FIG. 5 is an exemplary side view of Generation Three device 23. This view depicts arrangement of the spectrometer emitter digital board 16 and receiver digital board 17 on opposite sides of liquid test port 15 so that in operation, infrared light is transmitted through a sample on sample tray 14 when sample tray 14 is slid into port 15. This Figure also depicts optional locations on Generation Three device 23 for a battery 28, a battery recharge connection 29, USB connection port 30, and display screen 26.

Figure 6:
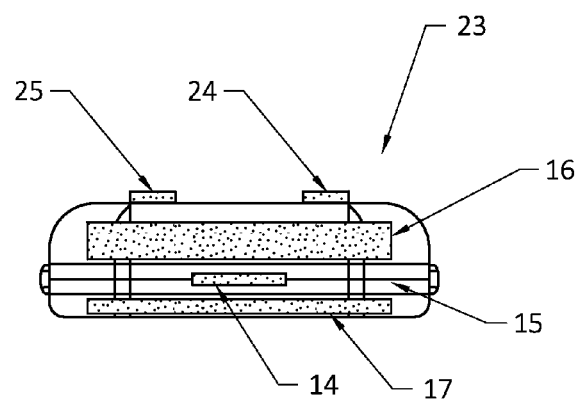
FIG. 6 depicts an exemplary front view of the spectroscopy device illustrated in FIG. 4.

FIG. 6 illustrates an exemplary front view of Generation Three device 23. This view depicts an optional arrangement of on/off button 24, test/send button 25, emitter digital board 16 and receiver digital board 17 in the configuration depicted in FIG. 5, with sample tray 14 in liquid test port 15.

Figure 7:
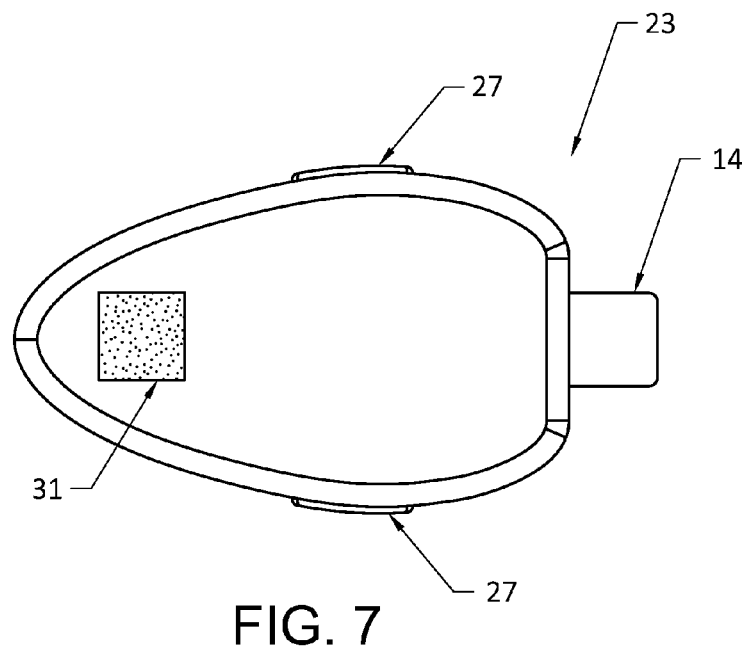
FIG. 7 depicts an exemplary bottom view of the spectroscopy device illustrated in FIG. 4.

FIG. 7 is an exemplary bottom view of Generation Three device 23 which illustrates optional placement of battery door 31 with respect to sample tray 14.

Figure 8:
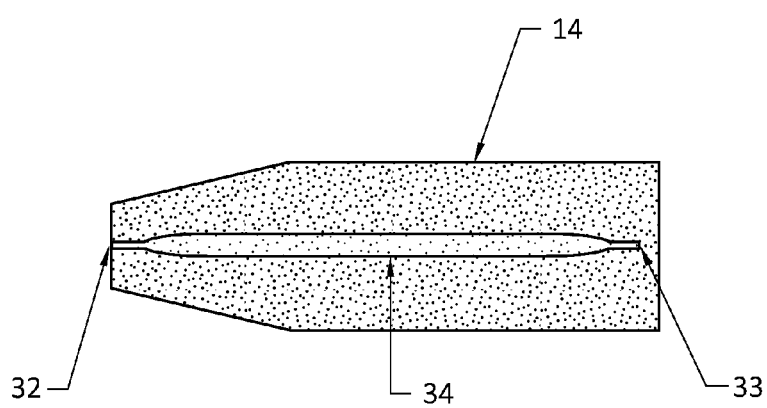
FIG. 8 depicts an exemplary top view of a sample tray according to the present invention.

FIG. 8 illustrates one embodiment of sample tray 14 according to the present invention. Sample tray 14 a sample uptake opening 32 that wicks the sample to be tested onto the tray, using capillary action. Sample tray purge vent 33, at the distal end of the sample tray 14 from the uptake opening 32, allows for filling. Preferably, the sample tray 14 is comprised of a polymer or other material that is naturally hydrophobic, so that a plasma based process will be used to enable the wicking of the liquid into the sample uptake well 34. Sample uptake well 34 holds the sample and provides a stable reservoir for infrared analysis of the sample.

Figures 9A, 9B:
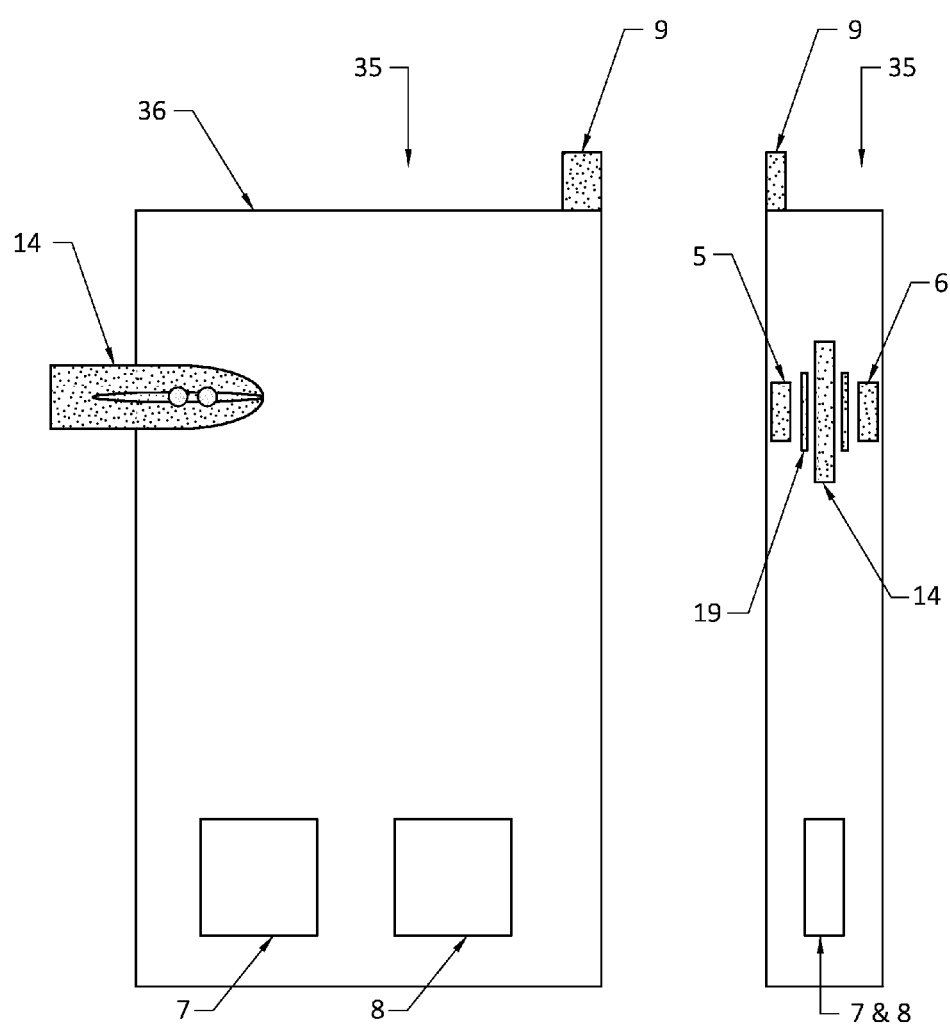
FIG. 9a is an exemplary front view of a spectroscopy device of the invention that is integral to a smart device, showing the sample tray inserted into the device.
FIG. 9b is an exemplary side view of the same device.

FIGS. 9a and 9b illustrate front and side views of a smart device 35 embodiment of the present invention. Sample tray 14 slides in and out of the smart device 35. FIG. 9b illustrates an exemplary arrangement of the spectroscopy components internal to the smart device 35, infrared light emitter 5, infrared light receiver 6, and two band pass filters 19. FIGS. 9a and 9b also show an exemplary data transmitter/receiver unit 9, and internal data processor 7, and GPS unit 8.

One or more infrared light filters 19 can be added directly to (e.g. formed as part of) the sample tray 14 (which may also be called a solution tray, solution receptacle, saliva solution tray, or insert tray) or in close proximity to sample tray 14. Sample tray 14 is moveable in relation to liquid sample port 15, but may be detachable or remain attached to smart phone 1, Generation Two device 10, Generation Three device 23 or smart device 35. Sample tray 14 is made of transparent material such as plastic, glass, Plexiglas, polyethylene and/or any other material transparent to spectrums of infrared light (so that the tray itself does not interfere with the IR testing. According to one embodiment, a PSA gasket can be used to define the channel that forms the uptake well 34, and a sheet of polymer film can be used to form a closed, cylindrical channel that makes up the uptake well 34. The height of the sample uptake well 34 may range from 20 microns to as high as 250 microns. The amount of liquid to be tested may range from 2 microliters to as high as 100 microliters. The width of the sample uptake well 34 may vary from 2 mm to as wide as 10 mm in width. The sample tray 14 many range in width from 5 mm to as wide as 20 mm and the length may range from 1 cm to as long as 6 cm. The height of the sample tray 14 may range from 0.5 mm to 3 mm. These dimensions are exemplary, and the uptake well 34, sample port 15, and other features of the device may be modified to properly conform to and work with any embodiment of the invention, including but not limited to Generation Two device 10, Generation Three device 23, smart phone 1, or smart device 35 in accordance with the present invention.

Figure 10:
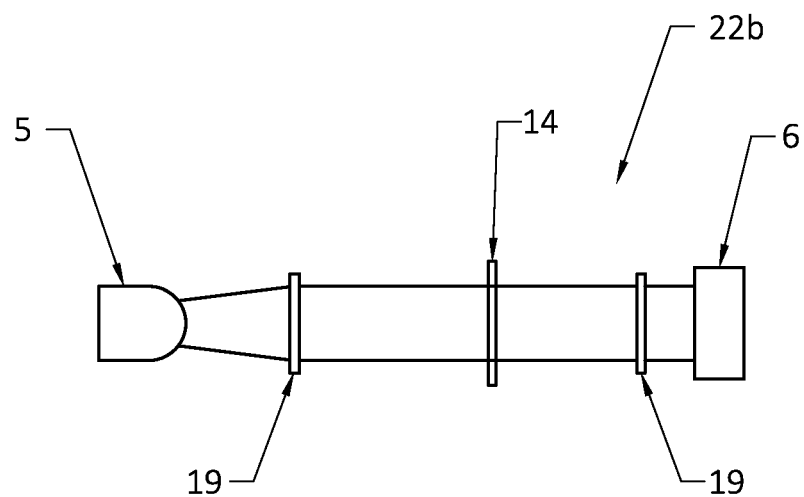
FIG. 10 depicts an exemplary arrangement of aspects of a spectrometer in accordance with the present invention.

FIG. 10 illustrates an in-line arrangement of a spectrometer 22b that may be utilized in an embodiment of the invention, including but not limited to those depicted in FIGS. 1 through 9. Photons from infrared light emitter 5 are transmitted through an infrared filter 19, then through the solution tray 14, a second infrared filter 19, and onto the infrared light receiver 6.

Figure 11:
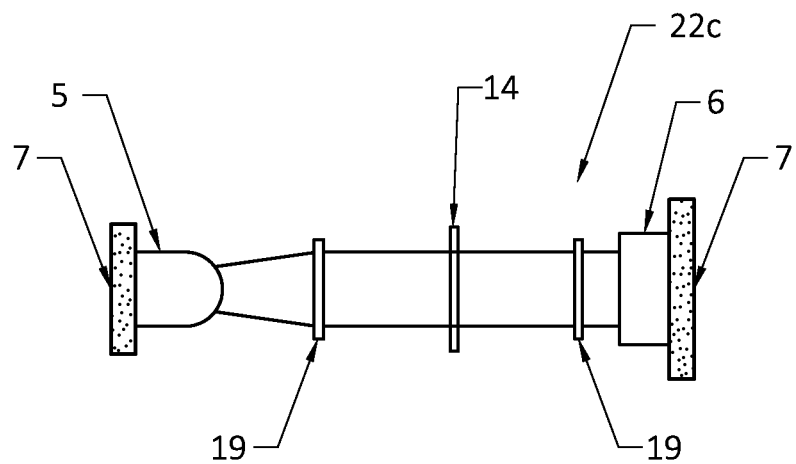
FIG. 11 depicts an exemplary arrangement of aspects of a spectrometer, including two infrared light filters and microprocessors, in accordance with the present invention.

FIG. 11 illustrates the in-line arrangement of a spectrometer 22c that incorporates a data processor 7 operably attached to each of infrared light emitter 5 and infrared light receiver 6. In this spectrometer 22c the photons also transmit from infrared light emitter 5 through an infrared filter 19, then through the solution tray 14, a second infrared filter 19, and onto the infrared light receiver 6.

Figure 12:
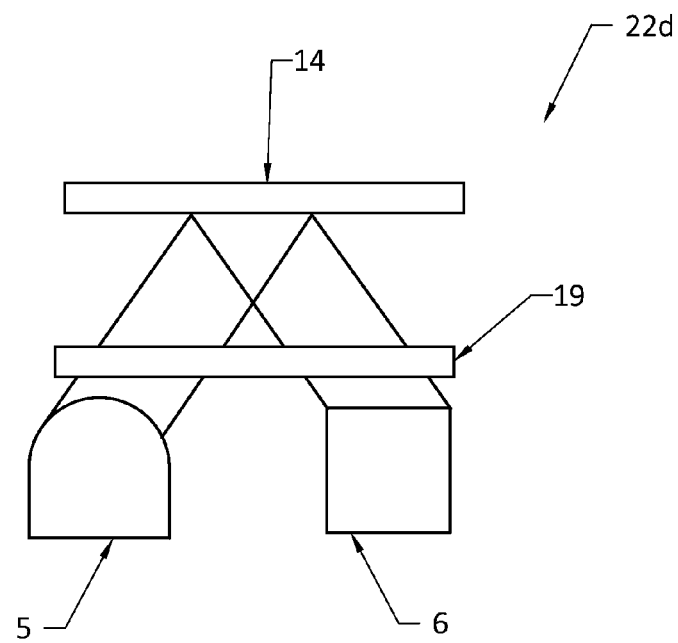
FIG. 12 depicts an exemplary arrangement of aspects of a spectrometer in a side-by-side configuration in accordance with the present invention.
Figure 13:
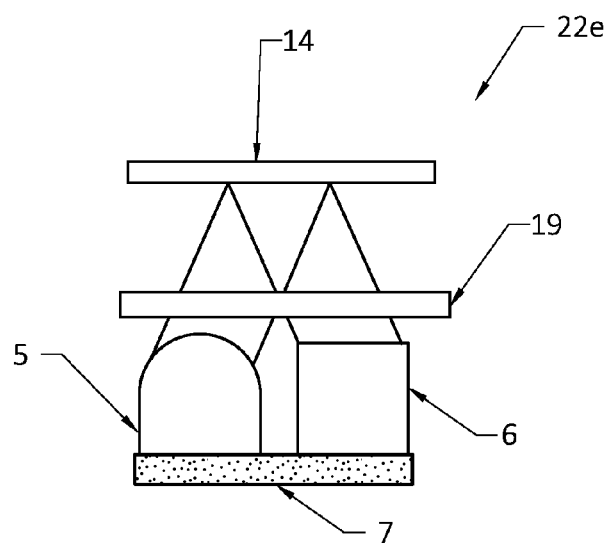
FIG. 13 depicts an exemplary arrangement of aspects of a spectrometer with attached microprocessors, in accordance with the present invention.

An alternative side-by-side arrangement of a spectrometer 22d is shown in FIG. 12. The infrared light emitter 5 and infrared light receiver 6 are in side-by-side configuration. Photons from an infrared light emitter 5 are transmitted through an infrared filter 19, then through a sample on the solution tray 14 where it is bounced off at an angle through an infrared filter 19, and onto infrared light receiver 6. FIG. 13 illustrates another side-by-side arrangement of a spectrometer 22c, where a data processor 7 is operably connected to each of the infrared light emitter 5 and receiver 6. The spectrometer 22e arrangement in FIG. 13 depicts what may also be called an 'on-chip' spectroscopy system. Photons from the infrared emitter 5 in FIG. 13 travel in a similar reflective manner to infrared receiver 6 as in FIG. 12.

The unique combination of the slideable sample tray 14 in close proximity to any of the spectrometer systems 22a, 22b, 22c, 22d or 22e shown in FIGS. 3, 10, 11, 12 and 13 integrated into one of the handheld/smart devices contemplated by the invention provides a quick and effective solution to accurate field IR spectroscopy testing of samples. As may be appreciated by those skilled in the art of IR spectroscopy, a further advantage of on-chip incorporation of the spectroscopy system 22e as shown in FIG. 13 is the ability of the system to switch between conventional radiant light readings and spectroscopy imaging by the movement or adjustment of other components on-chip rather than the external adjustments of spectroscopy system components.

The infrared light emitter 5 and infrared light receiver 6, as depicted in FIGS. 10 through 13 may have a calibration emitters 18, calibration receivers 19, and the calibration emitters 18 and calibration receivers 19 may have calibration band pass filters 21 to calibrate the device during use.

Figure 14:
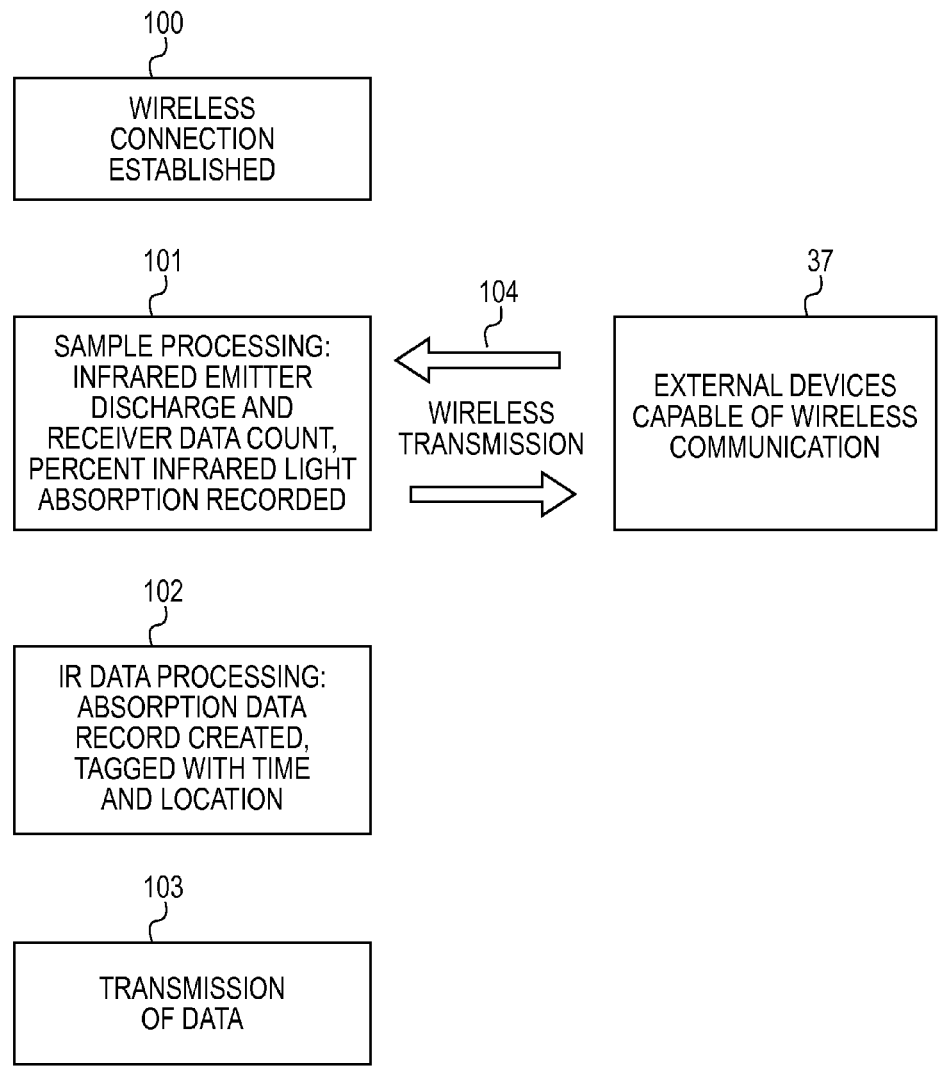
FIG. 14 depicts an exemplary flow chart of the IR spectroscopy method according to the invention.

FIG. 14 provides an illustrative flow chart of a method of the present invention. The spectroscopy device is either integral to a smart device or in wireless connection with the smart device so that wireless connection is established and wireless data transmission will be capable (100). A sample is placed in the liquid test port on the sample tray and is processed (101) wherein the infrared light emitter sends infrared light through the liquid sample, the infrared light receiver receives and records data associated with the wavelengths of infrared light absorbed by the sample. A processor in association with the infrared light receiver creates a data record and processes the data (102) which may include tagging the data record with additional location and/or time information. The data record is transmitted (103) via wireless communication to one or more external devices 37 capable of wireless communication for information, further analysis, processing, monitoring, recordkeeping, etc. Due to the wireless communication capability of the spectroscopy device, at any time during the process of testing the sample, wireless communications may be transmitted to and from the device to other computers or devices. For example, the spectroscopy device may query another device for: location, time, spectroscopic calibration data, and patient data. Additionally, the spectroscopy device may transmit data for storage, for example to a 'cloud' storage location.

Figure 15:
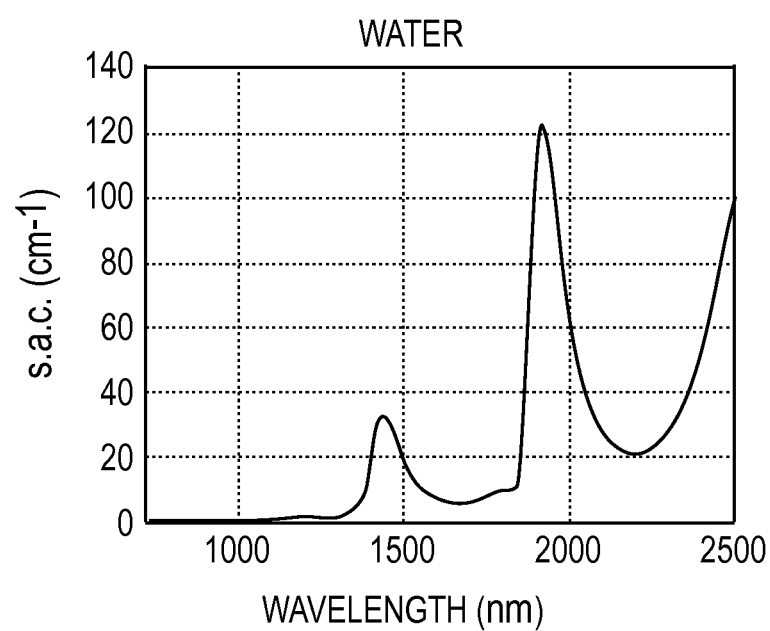
FIG. 15 depicts a spectral image of the near IR absorption of water.

FIG. 15 depicts an image of the near-IR absorption spectrum of water. Water exhibits prominent bands at 1.45 and 1.95 nm; there is an additional band near 2.9 nm which is at the upper end of the near-IR spectral region. Only the short-wavelength tail of that band is seen in FIG. 15. This is one example of the type of spectral image and data that may be generated using the spectroscopy device and method of the present invention.

Figure 16:
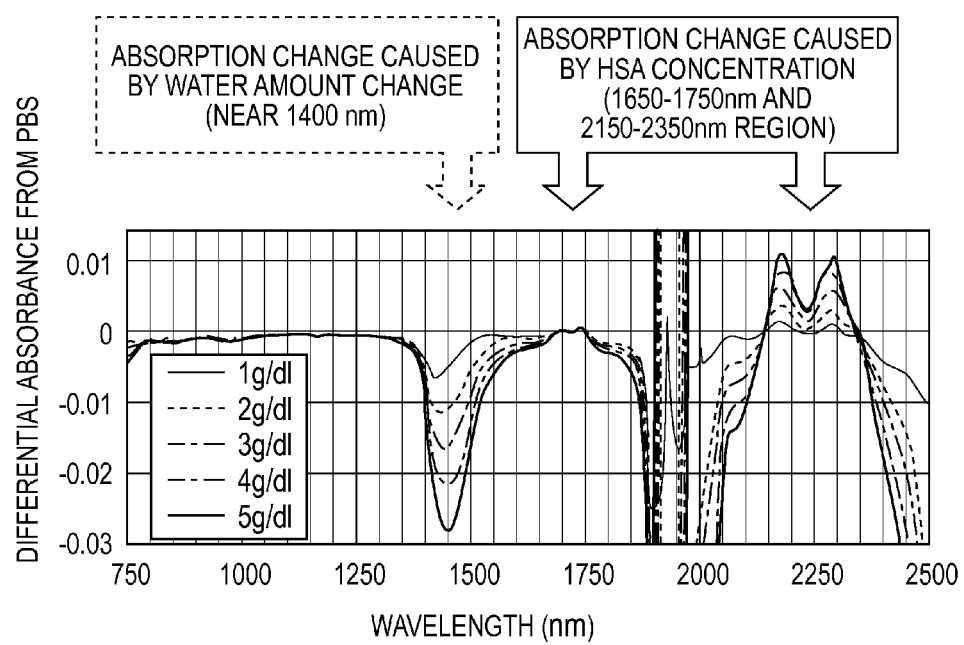
FIG. 16 depicts a spectral image of the near IR absorption of saliva.

FIG. 16 depicts an image of the near-IR absorption spectrum of HSA (human serum albumin) in water. The near-IR spectrum of saliva must take into account changes in the concentration of protein that could affect the absorption bands of small molecules. According to FIG. 16, HSA absorption occurs in the region from about 1650-1750 nm and about 2150-2350 nm. Other proteins would be expected to have slightly different near-IR spectrum but HSA is a good model for the effect of proteins in saliva. As water in the saliva absorbs strongly about 3000 nm, wavelengths below 3000 nm provide a good option for this test. This figure is another example of the type of spectral image and data that can be generated by the current invention.

Figure 17:
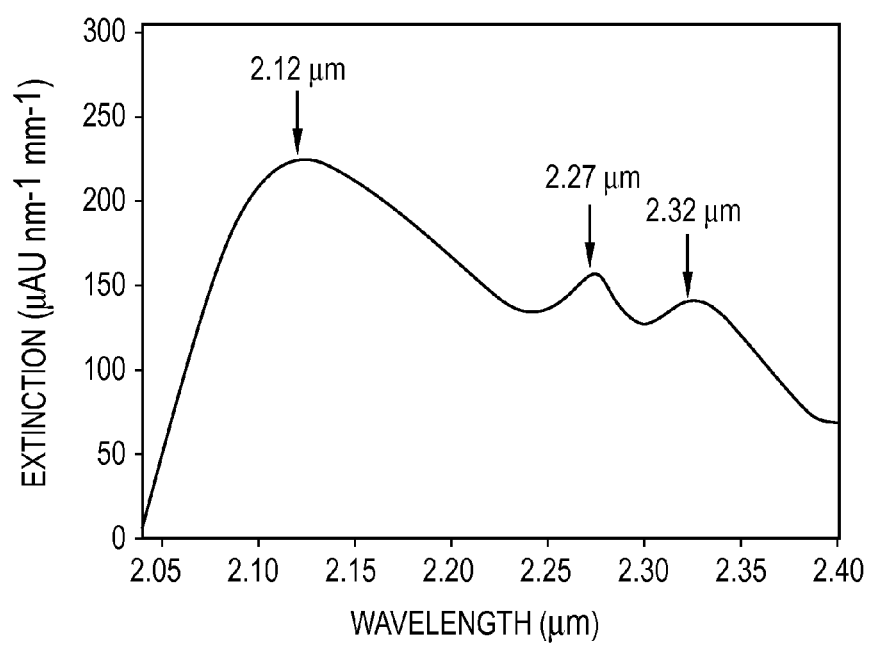
FIG. 17 depicts a spectral image of the near IR absorption of glucose.

FIG. 17 depicts an image of the near-IR absorption spectrum of glucose. The detection of glucose represents one of the most widely studies goals in clinical chemistry. There has been quite a large volume of work in this area with regard to near-IR detection. Most of the research in this area involves reflectance measurements (and especially transdermal measurements of glucose). FIG. 17 shows that the near-IR spectrum of glucose from 2.05 to 2.40 nm; the band at 2.27 nm was shown to be the best choice for quantitative analysis. A baseline near 2.30 nm should be used for this band.

Figure 18:
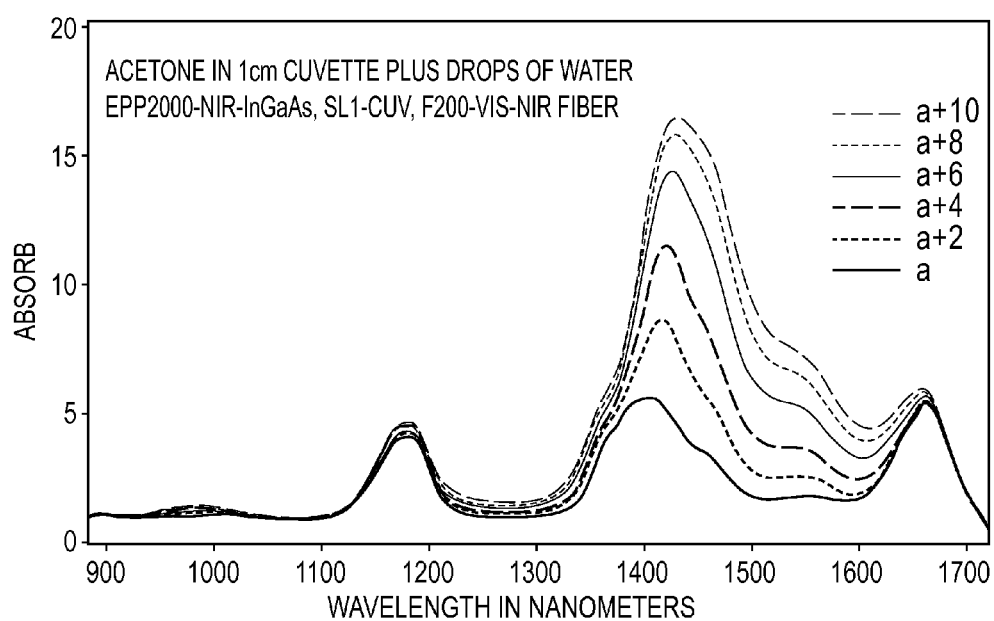
FIG. 18 depicts a spectral image of the near IR absorption of acetone with increasing quantities of water added.

FIG. 18 depicts an image of the near-IR absorption spectrum of acetone with increasing quantities of water, added dropwise. Acetone presents near-IR spectral bands that can potentially be used for detection in aqueous environments. While the spectrum in FIG. 18 does not show a good baseline point, it would be valuable to use a baseline point near 1.72 nm. There are other spectral bands (e.g. near 1.17 nm) that may also be of value in quantifying the acetone concentration. For this band, a baseline point at 1.10 nm would be appropriate. However, lipids and fatty acids have absorption bands near 1.165 and 1.21 nm, so this band should be taken as a secondary option to the band at 1.672 nm.

Figure 19A:
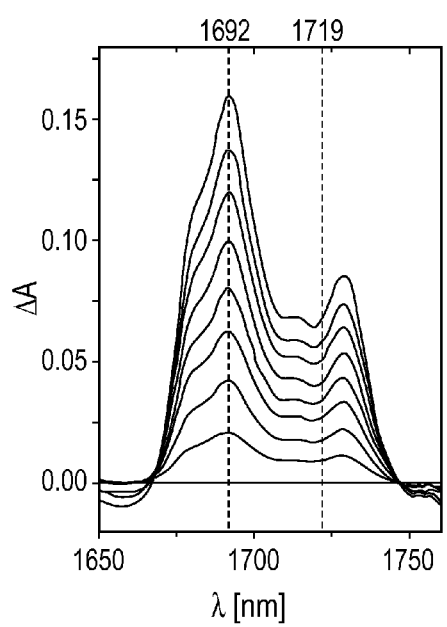
FIG. 19a depicts a spectral image of the near IR absorption of ethanol in water from 0-8%.
Figure 19B:
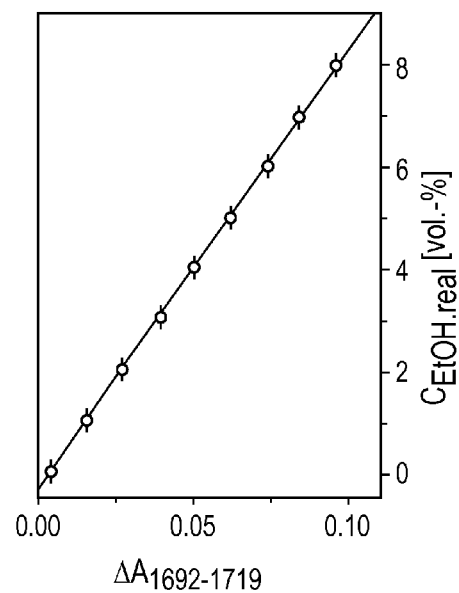
FIG. 19b depicts a calibration curve generated from the spectral image data.

FIG. 19 depicts an image of the near-IR absorption spectrum of ethanol in water from 0-8% with calibration curve generated from this data. Ethanol presents near-IR spectral bands that can potentially be used for detection in aqueous environments.

According to one example contemplated by the present invention, near-IR spectroscopy may be used to evaluate absorptions of analytes in serum. The primary analytes in serum are glucose, total protein, albumin, triglycerides, urea and cholesterol. The spectral region of glucose, for example, as measured by near-IR spectroscopy (and compared to reference standard) is typically about 2062-2353 nm. According to the method of the present invention, a serum (liquid) sample is placed on the sample tray, which is slideably inserted into the test sample port of the handheld IR spectrometer device. Infrared light is passed in close proximity through the sample to generate spectra data for the serum constituents, the data which is generated based on the wavelengths of IR light absorbed by the sample (and, conversely, the wavelengths transmitted through the sample). The IR spectrometer receives the data, and a processor processes the data into spectral data and/or imagery that identifies and quantifies the constituents in the sample, based on the optimal spectral wavelength absorption bands or regions. For example the optimal range for urea is a combination of ranges 1324 to 1800 nm and 2304 to 2370 nm; the optimal range for triglycerides were 1635-1800 nm and 2035-2375 nm, which would be identified and quantified by recording IR wavelength absorption in these band ranges In another example, a patient having diabetes may need glucose testing for regular monitoring or emergency testing. Glucose may be detected from saliva. A sample of saliva is quickly and easily placed on the sample tray, and inserted into the sample port in the handheld device in accordance with the invention. IR spectra are recorded by the spectrometer using a Fourier Transform infrared spectrometer (Perkin-Elmer, Fremont, Calif.). Strong infrared spectral bands are recorded at about 2850 $cm^{-1}$ and 2925 $cm^{-1}$ (using wavenumber as opposed to wavelength as the measurement) highlighting lipid groups in the saliva. Two prominent amide absorptions are recorded at 1655 $cm^{-1}$ and 1545 $cm^{-1}$. Glucose is detected at 950 to 1180 $cm^{-1}$. Because there are overlapping absorptions by the different constituents contained in the saliva, the spectrometer and microprocessor, using analytical methods common in the industry, are able to narrow the overlapping bandwidths and provide a correlation between the absorptions measured by the constituents in the saliva and absorption bandwidths already known—which provides a qualitative result identifying the nature of the analytes in the saliva, particularly the desired qualitative result for glucose.

According to another embodiment of the invention, IR spectra is recorded in the mid-IR range for analytes in solution such as drugs, e.g. cocaine. A saliva sample is deposited onto the sample tray, inserted into the device, a compact Fournier Transform IR spectrometer transmits near-IR light through the sample on the sample tray, and measurements within the narrow, ideal spectral range of 1760 to 1710 $cm^{-1}$ for the drug (in this case, cocaine) are performed. A specific IR bandwidth filter may be used to narrow down the spectral range used to identify and quantify the cocaine in the saliva sample. This method allows spectral analysis at the point of sample extraction, which may occur at a road-side DUI stop.

According to yet another example, saliva analysis is performed to evaluate constituents that exist and/or change in response to bodily stress, for example, exercise and sports. The IR spectrometer device of the present invention is extremely useful for field-ready, point of sample analysis of athlete saliva to evaluate psychological and physiological stress. Secretory immunoglobulin A (sIgA) is often used to study an immune response in the first instance to exercise. Additional biomarkers useful in evaluating bodily stress, which can be detected in saliva, are alpha-amylase, and cortisol. These biochemical components are identified in the mid-IR region (about 4000 to about 700 $cm^{-1}$), Fournier Transform infrared spectroscopy may be used to identify and quantify these biomarkers. In accordance with the current method, a small saliva sample is placed on the sample tray, the tray is slide into the port in the handheld device, and the sample is irradiated with mid-infrared light, absorption bands received by the receiving unit in the IR spectrometer, and said spectra wavelength data compared to calibration models to identify and quantify the biomarker levels. The data may be displayed in the device and/or transmitted wirelessly to one or more external devices, computers, etc. for further analysis, disease diagnosis (using other diagnostic tools), etc. This testing can occur at a training facility, sports arena, gym, locker room, etc.

With respect to data analysis and transmission, according to one embodiment of the invention, spectral images and data are preferably be transmitted via cellular or satellite telephone, internet link, or other telecommunication modality to another device, and similarly, data may be transmitted from one or more other devices to the spectroscopy device. The data may or may not include processed spectral images, and/ or user/patient/environmental sample identifiers such as name, sample number, sample type, date, time, location, etc. Alternatively, a small field of the total processed image/data is transmitted for reference, but not the entire image/data (e.g. but not limited to, for purposes of reducing the size of the data package transmitted from device to device). The data may be stored on the spectroscopy device for later upload to internal or external endpoints. The data may be transferred by wireless communication to a nearby computer, smart-device, data storage machine or other endpoint. Data and images may be encrypted for user/patient/environmental data protection, which encryption may use a public key for the user or organization using the device. Additional user/patient/environmental data may be downloaded over the telecommunications link after the initial record information is entered prior to a new sample test. In terms of remote transmission of images/ data, the present invention also contemplates the following aspects which may be carried out by a processor contemplated herein: (a) additional annotation of images/data with text, drawings, or graphics, (b) attaching data to other images transmitted to a smart phone or smart device integrated with the spectroscopy system (e.g. user/patient/environmental information, diagnosis, geographic information, time information, messaging, advertising information, warnings, or other content, etc.), and (c) further image/data processing for disease diagnosis, material safety, environmental analysis, etc.

The user of the spectroscopy system may be provided location-specific prompts, e.g. (but not limited to) prompts to select the patient record from a database of local patients, and/or prompted to visit or collect data from patients in the local area who are due for another test. This prompting ability allows for date and time sensitive analysis of human, animal, plant, or environmental conditions for health and safety monitoring. According to one embodiment, the spectroscopy device is equipped with standard or mobile web browsing capability.

Regarding portability, several factors serve to make the spectroscopy system even more useful as a portable device: use of infrared light-emitting diodes for illumination (eliminating the need for large or high-voltage power), use of low-power embedded computing systems to eliminate the need for a stand-alone associated computer system; use of low power infrared light emitters and receivers for liquid/solution analysis. The low-power nature of the system also allows for low battery weights (e.g. using lithium-ion batteries or other) in a system designed to operate for long (several hour) periods without connection to a power grid. Batteries may be single use or rechargeable. By creating this spectroscopy system using a smart phone or device or other portable handheld device, the size of the spectroscopy system is smaller than current high precision spectroscopy machines in the clinical or laboratory settings.

Uses contemplated for the spectroscopy system and method of the present invention include but are not limited to: remote or 'field' medical evaluation, treatment, health monitoring, drug detection and level monitoring (e.g. lithium levels, Depakote levels, Digoxin levels, etc.), drug abuse screening (e.g. personal, athletic competition monitoring, judicial/ court mandated drug screening, etc.), death, disability or health insurance screening, or other drug monitor programs. Some of these uses may further include biological or chemical assays, for example but not limited to, hematological analysis, blood counts, immunoassays, hormonal assays, examination or recording of tissue sample morphologies or pathology, blood, urine, saliva, bodily fluids, infectious fluids, cancerous fluids, bodily byproducts, toxins, or other biological medium analysis. The device and method may be used as part of a health or safety monitoring in food services environments, e.g. for inspection of surfaces for bacteria or the contamination of food or other products consumed by living entities.

Additional applications of the present invention include, but are not limited to analysis of environmental samples such as soil or water samples, such as standing water, pond, river, lake, ocean, for composition analysis and monitoring of microorganisms and/or contamination, etc.

The invention has been described in an illustrative manner, and the terminology used herein should not be construed as limiting the scope of the invention but as merely providing illustrations of embodiments of the invention. Therefore, it will be appreciated that the scope of the present invention fully encompasses other embodiments, and may be practiced otherwise than as specifically described. Reference to an element in the singular is not intended to mean "one and only one" unless explicitly so stated, but rather "one or more."

What is claimed is:

1. A method for determining a concentration of one or more compounds in a liquid sample, comprising:
   placing the liquid sample on a sample tray,
   inserting the sample tray into a sample test port housed in a handheld device containing an infrared spectrometer, the infrared spectrometer including:
      an infrared light source and an infrared receiver positioned at opposite sides of the sample tray,
      an infrared calibration emitter and an infrared calibration receiver positioned at opposite sides of the sample tray;

directing infrared light from the infrared light source at the sample and collecting the transmitted infrared light by the infrared receiver, thereby obtaining a sample spectrum;

directing infrared light from the infrared calibration emitter and collecting the transmitted infrared light by the infrared calibration receiver, thereby obtaining a calibration spectrum; and determining the presence or concentration of one or more compounds in the liquid sample based on a comparison between the sample spectrum and the calibration spectrum.

2. The method of claim 1 wherein the directed infrared light has a wavelength range of about 650 nm to about 15000 nm.

3. The method of claim 1 wherein the directed infrared light has a near-IR wavelength range of about 650 nm to about 3000 nm.

4. The method of claim 1 wherein the directed infrared light has a mid-IR wavelength range of about 3000 nm to about 8000 nm.

5. The method of claim 1 further comprising performing a calibration of the handheld device.

6. The method of claim 1 further comprising displaying the presence or concentration of the one or more compounds as spectral data and/or imagery on the handheld device.

7. The method of claim 1 further comprising transmitting the presence or concentration of the one or more compounds via wireless communication network to one or more other devices.

\* \* \* \* \*